(12) United States Patent
Liljegren et al.

(10) Patent No.: US 10,307,243 B2
(45) Date of Patent: Jun. 4, 2019

(54) DUAL MEMBRANE AIRWAY VALVE

(71) Applicant: SPIRATION, INC., Redmond, WA (US)

(72) Inventors: Erik Liljegren, Kirkland, WA (US); Clinton L. Finger, Bellevue, WA (US); Alexis Jensen, Redmond, WA (US)

(73) Assignee: SPIRATION, INC., Redmond, WA (US)

(*) Notice: Subject to any disclaimer, the term of this patent is extended or adjusted under 35 U.S.C. 154(b) by 192 days.

(21) Appl. No.: 15/432,023

(22) Filed: Feb. 14, 2017

(65) Prior Publication Data

US 2017/0281330 A1    Oct. 5, 2017

Related U.S. Application Data

(60) Provisional application No. 62/314,770, filed on Mar. 29, 2016.

(51) Int. Cl.
*A61F 2/04* (2013.01)
*A61B 17/12* (2006.01)
*F16K 1/44* (2006.01)
*A61F 2/24* (2006.01)

(52) U.S. Cl.
CPC .......... *A61F 2/04* (2013.01); *A61B 17/12104* (2013.01); *A61B 17/12172* (2013.01); *A61F 2/24* (2013.01); *A61F 2002/043* (2013.01); *A61F 2220/0016* (2013.01); *A61F 2220/0091* (2013.01); *A61F 2230/0093* (2013.01)

(58) Field of Classification Search
CPC ................ A61F 2/04; A61B 17/12104; A61B 17/12172; F16K 1/443
See application file for complete search history.

(56) References Cited

U.S. PATENT DOCUMENTS

| | | | |
|---|---|---|---|
| 6,692,494 B1 | 2/2004 | Cooper et al. | |
| 7,798,147 B2 * | 9/2010 | Hendricksen et al. | A61B 17/12022 128/200.24 |
| 8,454,708 B2 * | 6/2013 | Kutsko et al. | A61B 17/12022 128/200.24 |
| 8,603,127 B2 | 12/2013 | Alferness | |
| 9,622,752 B2 * | 4/2017 | Gonzalez et al. | A61B 17/12022 |
| 2008/0039786 A1 * | 2/2008 | Epstein et al. | A61B 17/12104 604/103.03 |
| 2015/0039021 A1 * | 2/2015 | Khairkhahan et al. | A61B 17/0057 606/200 |

(Continued)

FOREIGN PATENT DOCUMENTS

JP    2000-102545    4/2000

*Primary Examiner* — Kevin L Lee
(74) *Attorney, Agent, or Firm* — The Dobrusin Law Firm, P.C.

(57) ABSTRACT

A valve comprising: (a) a rod, (b) a plurality of struts in communication with the rod and extending generally radially outward away from the rod in a deployed state, the plurality of struts including at least: (i) a plurality of first struts that extend radially outward from the rod a first distance, and (ii) a plurality of second struts that extend radially outward a second distance from the rod, wherein the second distance is less than the first distance; and (c) one or more membranes that are in communication with the first struts, the second struts, or both.

24 Claims, 4 Drawing Sheets

(56) References Cited

U.S. PATENT DOCUMENTS

2015/0080903 A1   3/2015   Dillard et al.

* cited by examiner

DUAL MEMBRANE AIRWAY VALVE

FIELD

The present teachings generally relate to a valve that treats a structure such as an airway passageway and more specifically a mechanical airway valve that includes two more struts that treat an airway passageway.

BACKGROUND

Mechanical airway valves are placed within an airway to prevent air from flowing in selected portions of a lung.

It would be attractive to have a valve with two or more sets of struts for forming a seal with a passageway. What is needed is two or more sets of struts with different expansion radii so that a single valve can seal multiple different sized passages or irregularly shaped passageways. It would be attractive to have a valve with two or more membranes that contact the passageway to form a seal. What is needed is two or more membranes that form a seal with a passageway such that if one membrane does not form a complete seal a second membrane seals the passageway to form a complete seal between the two or more membranes.

SUMMARY

The present teachings meet one or more (if not all) of the present needs by providing A valve comprising: (a) a rod, (b) a plurality of struts in communication with the rod and extending generally radially outward away from the rod in a deployed state, the plurality of struts including at least: (i) a plurality of first struts that extend radially outward from the rod a first distance, and (ii) a plurality of second struts that extend radially outward a second distance from the rod, wherein the second distance is less than the first distance; and (c) one or more membranes that are in communication with the first struts, the second struts, or both.

The teachings herein surprisingly solve one or more of these problems by providing a valve with two or more sets of struts for forming a seal with a passageway. The teachings herein provide two or more sets of struts with different expansion radii so that a single valve can seal multiple different sized passages or irregularly shaped passageways. The teachings herein provide a valve with two or more membranes that contact the passageway to form a seal. The teachings herein provide two or more membranes that form a seal with a passageway such that if one membrane does not form a complete seal a second membrane seals the passageway to form a complete seal between the two or more membranes.

DETAILED DESCRIPTION

Figure 1:
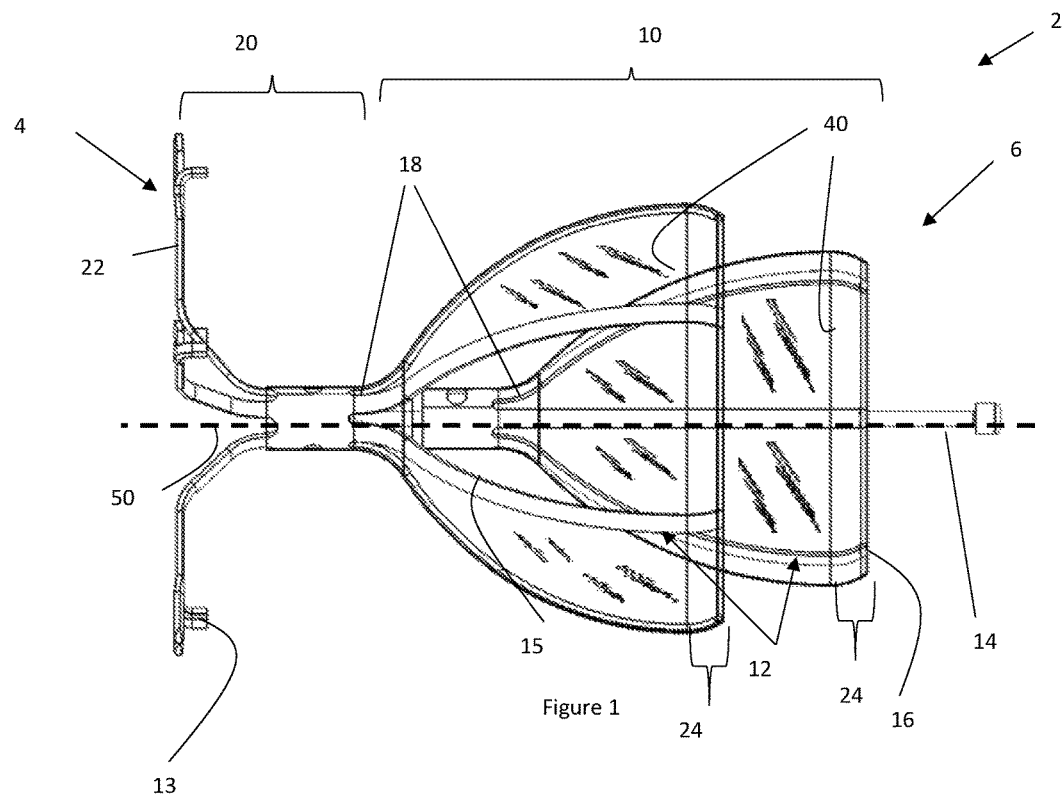
FIG. 1 illustrates a plan view of a valve of the teachings herein.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide an improved valve. The present teachings provide an improved airway valve. The valve functions to gradually open in an airway and block airflow through that airway. The valve may seal one or more structures such as passageways in a lung. Preferably, the valve forms a seal and prevents airflow in a bronchi, a bronchiole, a branch of a bronchi, a branch of a bronchiole, or a combination thereof. The valve may function to be removable. The valve may function to be biocompatible. The valve may extend along an axis. The valve may curve. The valve may be linear. The valve may bend in one or more locations, one or more directions, or both. The valve may bend and be rotatable. The valve may include one section. The valve may include a plurality of sections. The valve includes a distal end and a proximal end. The valve includes a longitudinal axis that extends from the distal end to the proximal end. The longitudinal axis may follow the shape of the valve such that the longitudinal axis is linear, arcuate, includes bends, or a combination thereof. Preferably, the longitudinal axis is a largest dimension of the valve and extends parallel to a length of the valve.

The distal end may be the lead end and/or first end placed into an airway. The distal end may include a fixed anchor. The distal end may include a terminal point, be a terminal end, or both. The distal end may include one or more blunt features so that during deployment, the distal end contacts a wall of the airway and moves the airway while the airway remains intact. If more than one valve section is present then each valve section may include a distal end. The distal end may be located opposite the proximal end. One or more of the distal ends of a valve section may be in communication with a proximal end of an adjacent valve section.

The proximal end may be the last end to be deployed. The proximal end may include one or more retraction features. The proximal end may include one or more removal features. The proximal end may include a rod.

The rod may be used to remove the valve from a structure. The rod may release the connection with the walls of the passage and/or airway. The rod may move the struts so that the struts are relaxed from the deployed state and the valve can be moved and/or removed. The proximal end may include a bulbous portion, a hook, a hole, a "J" shape, or a combination thereof that assists in forming a connection so that the valve may be removed. The proximal ends may include one or more hinge points, one or more interconnects, or both. The valve may include more than one proximal end when the valve includes more than one valve section. The valve may include two or more sections and even a plurality of sections.

The one or more sections may function to individually seal an airway or anchor to an airway. The one or more sections may function to seal a length of a passage, an airway, or both. Each of the one or more sections may be movable relative to one another. The one or more sections may be located along an axis. The one or more sections may be located end to end. The one or more sections may be located at an angle relative to each other (i.e., in a non-straight line). The one or more sections may connect to a passage or an airway. The one or more sections may be substantially identical. One section may be a valve section that includes struts and a second section may be an anchor section that includes anchors. The one or more sections may be movable along a rod, fixed to a rod, or both. Two or more sections may be connected to a single rod (i.e., one unitary piece). Each section may be connected to its own rod. Each section may have a cross-sectional length (e.g., diameter (i.e., a distance radially outward from the rod)) in the fully deployed state of about 5 mm or more, about 6 mm or more, about 7 mm or more, about 8 mm or more, or even about 9 mm or more. The sections may have a cross-sectional length in the fully deployed state of about 20 mm or less, preferably about 15 mm or less, or more preferably about 12 mm or less. The sections may each have multiple cross sectional lengths. Preferably, the valve sections include multiple cross-sectional lengths. More preferably, each group of struts include a cross-sectional length and the cross-sectional lengths are different. The one or more sections may be a valve section, an anchor section, or both.

The one or more valve sections may function to seal an airway or a portion of an airway. The one or more valve sections may function to work together to complete seal an airway. Each valve section may include two or more struts and preferably a plurality of struts. More preferably, each valve section includes two or more sets of struts (e.g., a first set of struts and a second set of struts). Each valve section, each set of valves, or both may include two or more struts, three or more struts, four or more struts, preferably five or more struts, or even six or more struts. Each valve section may include one set of struts. Preferably, each valve section includes two or more sets of the struts.

Each set of struts may function to work together to seal all or a portion of an airway (seal as discussed herein means prevent air from passing beyond the valve). Each set of struts may include two or more struts, three or more struts, four or more struts, preferably five or more struts, or even six or more struts. The struts may be evenly distributed about the rod, the base member, or both. The struts may be asymmetrically distributed about the rod, the base member, or both. One set of struts may be aligned with another set of struts. One set of struts may be offset relative to another set of struts. For example, a first set of struts may include struts that are located in-between a second set of struts. One or more sets of struts may include a membrane. One set of struts may be free of a membrane. One set of struts may support the membrane when a first set of struts is compressed to a point where the membrane includes wrinkles or is not in contact with a passageway to seal a passageway. Both set of struts may include a membrane. One set of struts may be located fully and/or partially inside of another set of struts. One set of struts may extend longitudinally forward beyond a second set of struts. One set of struts may extend radially outward further than a second set of struts (i.e., extend further outward from a rod). For example, one set of struts (e.g., internal struts) may be located at least partially internal to a second set of struts (e.g., an external set of struts).

The struts may function to expand the membrane. The struts may function to move the membrane into contact with a structure (i.e., a passageway or an airway). Preferably, the struts may function to move the membrane radially outward. The struts may be movable so that a force applied by the struts may be increased or decreased at a predetermined location. Each valve section and the struts may exert a sufficient force on a passage or airway to form a seal with the passage or airway. Each valve section and the struts may exert a sufficient force so that a passage and/or airway is blocked by a membrane in communication with the struts. The struts of each valve section may exert an outward force of about 0.01 Kg or more, about 0.04 Kg or more, about 0.06 Kg or more, or even about 0.08 Kg or more. Each strut may exert a force of about 1 Kg or less, about 0.5 Kg or less, about 0.25 or less, or even about 0.1 Kg or less. The struts may function to expand so that the struts and membrane seal an airway, a passageway, or both. The struts may function to elastically deform from a closed position (i.e., a retracted state) to an open position (i.e., deployed state). The struts may extend from being located along the longitudinal axis to extending radially outward. The one or struts may be formed into an open position and then closed until deployed where the struts elastically deform into the open position. Each strut may extend generally radially outward from a base member, a rod, or both. The struts may extend radially outward from the rod a distance of about 1 mm or more, about 2 mm or more, or about 3 mm or more. The struts may extend radially outward from the rod a distance of about 8 mm or less, about 6 mm or less, or about 4 mm or less. One set of struts may extend radially outward a larger distance than a second set of struts (e.g., one set of struts may extend outward a distance of about 1 mm or more, about 1.5 mm or more, about 3 mm or less than a second set of struts). When more than one set of struts are present a second set of struts may extend radially outward less than a first set of struts. A second set of struts may extend radially outward from the rod a distance that is about 90 percent or less, about 80 percent or less, about 75 percent or less, or about 60 percent or less than the first set of struts. A second set of struts may extend radially outward from the rod a distance that is about 30 percent or more, about 40 percent or more, about 45 percent or more, or about 50 percent or more than the first set of struts. Each strut may form a "J" shape. Each strut may include one or more bends, two or more bends, or even three or more bends. Each strut may curve so that the strut extends radially outward from the base member. The strut as it extends outward from the base member may curve so that the angle relative to the base member extends away from the rod, the base member, or both and then parallel to the rod. Each strut in a fully relaxed state may have at least a section that is parallel with a base member, a rod, or both. The struts have a length. Each of the struts may have an identical length. The length of the struts from valve section to valve section, from strut set to strut set, or both may vary or be the same. For example, the valve sections (or set of struts) at the distal end may have shorter struts then the valve sections at the proximal end so that the distal end may fit within or seal smaller passages and/or airways. Each strut may have a total length of about 3 mm or more, about 4 mm or more, or even about 5 mm or more. Each strut may have a total length of about 10 mm or less, about 9 mm or less, or about 8 mm or less. For example, one set of struts may have a length of about 5 mm and a second set of struts may have a length of about 7 mm. The length of a first set of struts to a second set of struts may be about 90 percent or less, about 80 percent or less, about 75 percent or less, or about 60 percent or less than the second set of struts or vice versa. The length of a first set of struts to a second set of struts may be about 30 percent or more, about 40 percent or more, about 45 percent or more, or about 50 percent or more than the second set of struts or vice versa. Each strut may include one or more features for gripping tissue, a wall of a passage, a wall of an airway, or a combination thereof. Each strut may have a tip that curves inward, that extends towards the rod, or both. The struts may be made of any elastically deformable material. The struts may be made of a biocompatible material. The struts may be made of metal, plastic, polymeric material, an alloy, or a combination thereof. Preferably the struts may be made of nitinol (i.e., a nickel titanium alloy). Some struts may be directly connected to a rod and some struts may be connected to a base member and the struts may be connected to a membrane that extends between the struts and along the struts from the tip to the rod.

The membrane may function to prevent passage of fluids. The membrane may function to restrict airflow through a structure, a passageway, and preferably an airway. The membrane may be fluid impermeable. The membrane may be rigid. The membrane may be flexible. The membrane may be plastically deformable. Preferably, the membrane is elastically deformable. The membrane may be attached along a length of each strut. The membrane may be attached at one or more points on each strut. The membrane may substantially surround all or a portion of a strut (i.e., from the rod to the tip of each strut). The membrane may be in communication with one set of struts. The membrane may be located on one set of struts and contacted by a second set of struts if the membrane is restricted so that the struts are not fully deployed (i.e., deployed to about 95 percent or less, about 90 percent or less, about 85 percent or less, or about 80 percent or less than full deployment). The membrane may be fully supported on one set of struts and then moved into contact with a structure to form a complete seal by a second set of struts moving the membrane into contact with the structure. Each set of struts may include a membrane. Each set of struts may individually move a membrane into contact with a surface so that each set of struts and respective membrane form a seal with the surface. The membrane may be made of a polyurethane, an aliphatic polycarbonate-based thermoplastic polyurethane, a polyethylene siloxane, a material that includes silicone, a silicone polyurethane, a fluoroelastomer, an acrylate polymer, a polyacrylate, or a combination thereof. The membrane may be made of a material with a modulus of elasticity of about 10 GPa or less, about 5 GPa or less, about 2 GPa or less, or even about 1 GPa or less. The material may have a modulus of elasticity of about 0.001 GPa or more, about 0.003 GPa or more, about 0.005 GPa or more, about 0.01 GPa or more, about 0.03 GPa or more, about 0.05 GPa or more, or even about 0.06 GPa or more. The material of the membrane may have a modulus of elasticity of from about 0.00100 GPA to about 0.065 GPa. A material with a tensile stress at 100 percent strain of about 3 MPa or more, about 5 MPa or more, or more preferably about 8 MPa or more, about 12 MPa or more, about 15 MPa or more, or even about 20 MPa or more. The material may have a tensile stress at 100 percent strain of about 100 MPa or less, about 50 MPa or less, or about 30 MPa or less. A material with a tensile stress at 200 percent strain of about 4 MPa or more, about 7 MPa or more, about 10 MPa or more, about 15 MPa or more, or about 20 MPa or more. The material may have a tensile stress at 200 percent strain of about 100 MPa or less, about 50 MPa or less, or about 30 MPa or less. A material with a tensile stress at 300 percent strain of about 6 MPa or more, about 9 MPa or more, about 13 MPa or more, about 18 MPa or more, or about 20 MPa or more. The material may have a tensile stress at 300 percent strain of about 100 MPa or less, about 50 MPa or less, or about 30 MPa or less. A material with a tensile strength at break of about 15 MPa or more, about 20 MPa or more, or about 25 MPa or more (i.e., between about 15 MPa and about 30 MPa). The material may have a tear strength of about 40 kN/m or more, about 60 kN/m or more, about 75 kN/m or more, about 100 kN/m or more. The material may have a tear strength of about 200 kN/m or less, about 150 kN/m or less, or about 125 kN/m or less. When more than one membrane is used, one membrane may be elastic and one membrane may be non-flexible. For example, one membrane may be made of a thermoplastic polyurethane and one membrane may be made of a silicone polyurethane. The membrane may stretch without wrinkling. The membrane may be stretched by a force of the struts expanding from a retracted state to a deployed state. The membrane may be connected to a set of struts, a base member or both. The two or more struts and preferably a plurality of struts may be connected to a base member.

The base member may connect the struts to a rod. The base member and the struts may be one integral piece. Each of the base members may function to axially move along a rod. The base members may function to axially restrict one end of a strut. The struts may be fixedly connected to the base member (e.g., welded, adhesively bonded, or both). Each set of struts may include a base member. Two or more sets of struts may be connected to a single base member. The base member may lock to a rod. The base member may move along a rod. The base member may be movable to allow the struts to expand radially outward. Some base members may be axially movable, radially movable, or both and some base members may be static or immoveable. The base members may be generally toroidally shaped, doughnut shaped, or both. The base members may be cylindrical. The base member may include a through hole that a rod extends through.

The one or more anchor sections may function to prevent movement of the valve when the valve is in the deployed state. The one or more anchor sections may function to prevent movement of one or more valve sections, one or more rods, the entire valve, or a combination thereof. The one or more anchor sections may function to prevent movement of the valve within a passage, an airway, or both so that the valve remains at a desired location. The one or more anchor sections may prevent axial movement of a valve section relative to a rod. The one or more anchor sections may be located at the distal end, the proximal end, or both ends of the valve. The one or more anchor sections may be located in a middle section of the valve. Preferably, the one or more anchor sections may be located at the distal end of the valve. The one or more anchor sections may include one or more arms that attach the valve to a structure, prevent movement of the valve, or both.

The one or more arms may function to connect the valve to a structure. The one or more arms may function to prevent movement of the valve when the valve is deployed. The one or more arms may extend radially outward from a rod. The one or more arms may include a segment that extend outward from the rod at an angle of about 45 degrees or more, about 60 degrees or more, about 75 degrees or more, or about substantially 90 degrees. The one or more arms may extend outward from the rod at an angle of about 160 degrees or less, about 135 degrees or less, or about 105 degrees or less. The one or more arms may be made of the same material as the struts. The one or more arms may be made of nitinol, steel, surgical steel, stainless steel, plastic, a polymer, a thermoset, a thermoplastic, or a combination thereof. The one or more arms may include one or more anchor tips that connect to a structure (e.g., tissue of a structure).

The one or more anchor tips may function to grip a structure, anchor to a structure, or both. The one or more anchor tips may function to prevent the arms form moving relative to a structure. The one or more anchor tips may function to prevent movement of the arms relative to the structure. The one or more anchor tips may extend into a structure, a passageway, tissue, or a combination thereof. The one or more anchor tips may have a tip that is pointed, blunt, rounded, flat, at an angle relative to the arms, or a combination thereof. The one or more anchor tips may extend outward beyond the main portion of the arms. The one or more anchor tips may be angled towards a distal end, a proximal end, or both. Some anchor tips may extend at an angle relative to the arms, and some anchor tips may extend coplanar with the arms. The anchor tips may have a length of about 1 mm or more, about 2 mm or more, or about 3 mm or more. The anchor tips may have a length of about 10 mm or less, about 8 mm or less, or about 5 mm or less. The one or more anchor tips and arms may extend outward from the one or more rods.

The one or more rods may function to support a section, multiple sections (e.g., a valve section and an anchor section), one or more strut sets, two or more strut sets, or a combination thereof relative to one another. The one or more rods may extend along a longitudinal axis of the valve, may be the longitudinal axis of the valve, or both. The one or more rods may function to allow the valve or sections to be placed within a passage and/or airway, removed from a passage and/or airway, or both. The one or more rods may function to permit movement of the sections relative to one another. The one or more rods may include one or more curves, one or more bends, or both. Preferably, the one or more rods may be generally straight (i.e., linear). The one or more rods may be hollow, solid, or both. The one or more rods may be flexible. The one or more rods may be made of nitinol, steel, surgical steel, stainless steel, plastic, a polymer, a thermoset, a thermoplastic, or a combination thereof. The one or more rods may be movable in one direction to assist in centering the valve within a passageway and especially a structure. The one or more rods may include through holes, dimples, indentations, recesses, raised sections, non-linear sections, or a combination thereof. The one or more rods may each include a distal end and a proximal end. The distal end, the proximal end, or both may include one or more connection features, one or more removal features, one or more detachable features, or a combination thereof. The valve may include a plurality of rods that are connected together by one or more hinge points so that the valve may move through a non-linear path (e.g., a tortuous path).

The one or more hinge points may function to permit two or more of the sections to move relative to one another. The one or more hinge points may allow rotational movement, angular movement, or both. The one or more hinge points may allow one section to bend around a curve while another section is generally straight. The hinge points may allow for adjacent sections to move out of a straight longitudinal axis. For example, one section may move up, down, left, right, diagonally, at an angle, or a combination thereof relative to an adjacent section. The one or more hinge points may be located between a distal end of one section and a proximal end of an adjacent section. The one or more hinge points may allow for two or more, three or more, or even four or more degrees of freedom of one section relative to an adjacent section. The one or more hinge points may be connectable and disconnectable while the valve is located within a passage or airway. The one or more hinge points may be released by accessing a feature at a proximal end of the valve (i.e., the end closest to an exit). The one or more hinge points may have a portion that extends from a distal end to a proximal end that may be disconnected so that one of the plurality of sections may be removed from an airway while the rest remain within the airway. The one or more hinge points may be a coil spring. When one of the sections is removed, the hinge point of the next adjacent valve section may be used to remove the entire valve. The hinge points may include two or more interconnects (i.e., one interconnect extending from each valve section).

The one or more interconnects may function to form a connection between two adjacent sections so that a hinge point is created. The one or more interconnects may function to connect a distal end of one valve section to a proximal end of an adjacent valve section. The one or more interconnects may be a hole through a rod. The one or more interconnects may be one or more wires that are connected to and extend from a rod. The one or more interconnects may be a magnetic coupling. The one or more interconnects may be a hitch and ball or ball and socket. The one or more interconnects may be interlocking loops. The one or more interconnects may be interconnected rings, loops, hooks, or a combination thereof. One or both of the adjacent interconnects may be permanent, releasable, or both. One or both of the adjacent interconnects may be releasable from a proximal end, an end opposite the interconnect, or both. One or both of the interconnects may include a weakened point that is breakable by axial movement, twisting, or both. The one or more interconnects may assist the strut in moving along a longitudinal axis and to extend out of a longitudinal axis.

The deployed state may function to seal a passage, an airway, or both. The deployed state may function to extend the struts radially outward to support a valve substantially within a center of a passage and/or an airway. The deployed state may have the struts fully deployed and the movable anchors moved to a steady state (i.e., fully deployed location) where further movement of the valve does not occur. The deployed state may have the struts extending radially outward. The fully deployed state may have the struts extending outward from the rod and into contact with a structure such as a passageway. The struts may be restricted from fully opening due to the structure such that a steady state is not achieved. The struts may gradually extend from the retracted state to the fully deployed state and may extend at an angle less than 90 degrees. The valve may slowly transition from a retracted state to a fully deployed state over time as the struts elastically deform back to a steady state shape (i.e., fully deployed state). The struts, the anchors, or both may progressively open from the retracted state to the deployed state over a period of time (e.g., 6 hours or more, 12 hours or more, 24 hours or more, 1 day or more, 3 days or more, or even 1 week or more) so that a passage, airway, or both is progressively sealed as the struts fully open. The struts, the anchors, or both may rapidly open into contact with the structure such as a passageway (e.g., 5 minutes or less, 3 minutes or less, 1 minute or less, or even 30 seconds or less).

The retracted state may have the valve located within a capsule, a cartridge, a catheter, a bronchoscope, or a combination thereof. The retracted state may have the struts, anchors, or both extending substantially parallel to the longitudinal axis. The retracted state may have the struts, anchors, or both pointing away from the distal end, towards, the proximal end, or both. The retracted state may have the struts, anchors, or both pointing in a direction so that during placement the struts do not inadvertently connect to any passages, walls, tissue, or a combination thereof. The retracted state may have the valve compacted so that the valve may travel through one or more passages, one or more air ways, a catheter, a bronchoscope, or a combination thereof. The retracted state may allow the valve to travel through tortuous passages, airways, or both without connecting to the walls, tissue, or both. The retracted state may allow the valve to be placed in a second division, a third division, or even a fourth division of the airway tree. The retracted state may be ended once the valve is ejected from, released from, removed from, or a combination thereof a capsule, a cartridge, a catheter, a bronchoscope, or a combination thereof.

The valve may be loaded into a cartridge so that the struts are maintained is a folded configuration, a parallel relationship to the longitudinal axis, or both. The valve may be ejected from the cartridge so that any pressure on the struts by the cartridge is released. The endoscope, bronchoscope, or both may be pulled backwards as the cartridge, valve, or both are released so that the valve is placed within a passage, an airway, or both. The endoscope, bronchoscope, or both may be pulled back so that the valve is maintained in a desired location, a predetermined location, at a collapsed location, or a combination thereof. Once the valve is deployed the struts may function to begin elastically deforming. The struts may be configured so that the struts sea; a passage, an airway, or both as the struts elastically deform. The struts may be connected to the anchor and may form a connection with a passage, tissue, airway, a wall, or a combination thereof so that axial movement of the strut is substantially prevented.

FIG. 1 illustrates a side view of a valve 2. The valve 2 includes a distal end 4 and a proximal end 6. The valve 2 includes a valve section 10 and an anchor section 20. The valve section 10 includes a plurality of struts 12. The struts 12 as shown are arranged in two groups. The first group or set is first strut section 15 and the second group or set is a second strut section 16 that are located inside of the first strut section 15. A membrane 40 extends over the plurality of first strut section 15 and the plurality of first strut section 15 expand the membrane 40 (shown in transparent so that the struts 12 are visible) to form a seal at the seal section 24 with a wall of a second passageway (not shown) of a patient. The second strut section 16 each include a membrane 40 and expand the membrane to form seal at a seal section 24 with the wall of the second passageway (not shown). The struts 12 are carried on a base member 18 that is in communication with a rod 14 that assists in placing the valve 2 in the passageway. The anchor section 20 includes a plurality of arms 22 that extend outward. The arms 22 include one or more anchor tips 13 that contact the wall of the second passageway (not shown) and assist in holding the valve in place. A longitudinal axis 50 extends along the length of the rod 14 and the valve 2.

Figure 2:
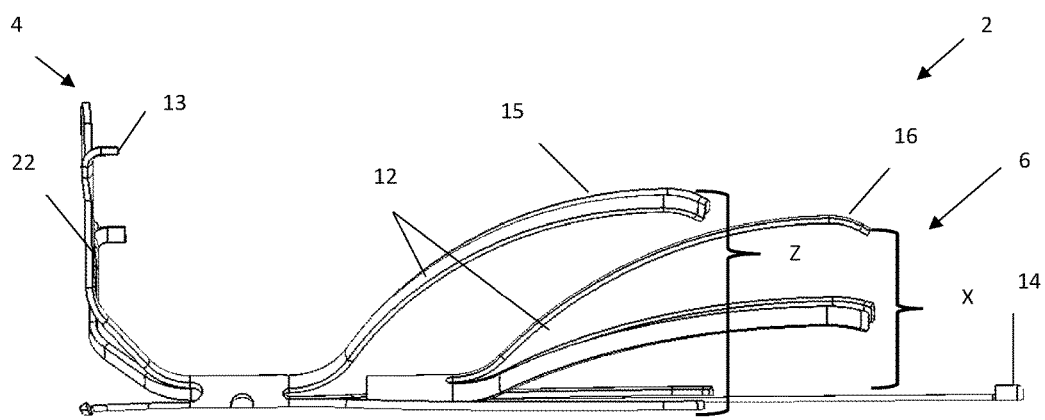
FIG. 2 illustrates an elevational view of half of a valve.

FIG. 2 illustrates a partial side view of a valve 2. The valve 2 includes a rod 14 that extends between a distal end 4 and a proximal end 6. Struts 12 are connected to (directly or indirectly) the rod 14 and extend radially outward from the rod 14. The struts 12 in the proximal end 6 arc outward and away from the rod 14 generally towards the proximal end 6. The first strut section 15 extend so that a tip of the first strut section 15 is located a distance (Z) from the rod 14 and the plurality of second struts extend so that the tip is located a distance (X) from the rod 14. As shown the distance (Z) is greater than the distance (X). A membrane (not shown) is connected to and extends from first strut section 15 and optionally a membrane may be connected to the second strut section 16. On the distal end 4 the valve 2 includes arms 22 with anchor tips 13 that anchor the valve 2 with an internal passageway.

Figure 3:
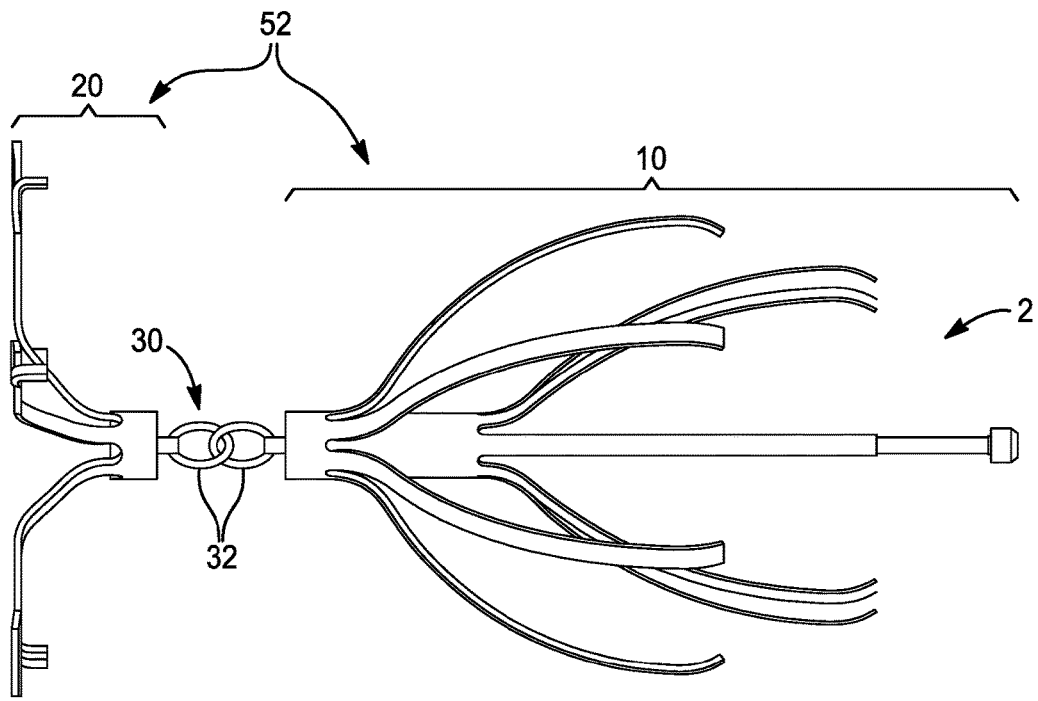
FIG. 3 illustrates an elevational view of a valve with a hinge.

FIG. 3 illustrates a side view of a valve 2 that has two sections 52 connected together. The two sections are movable relative to each other so that the sections can comply to mirror a shape of an internal passageway. The two sections are a valve section 10 and an anchor section 20 that are connected by a hinge point 30. The valve section 10 includes an interconnect 32 and the anchor section 20 includes an interconnect 32 and the interconnects are connected together to form the hinge point 30 so that the valve section 10 and the anchor section 20 are movable relative to each other.

Figure 4:
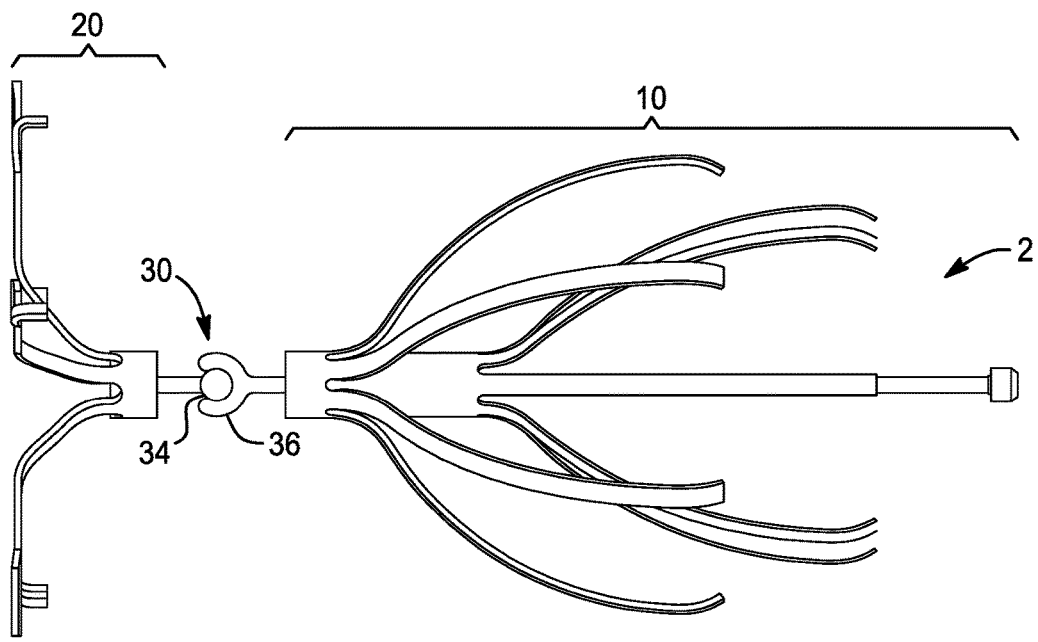
FIG. 4 illustrates an elevational view of a valve with a hinge.

FIG. 4 illustrates a side view of a valve 2 including a valve section 10 and an anchor section 20 that are connected together by a hinge point 30. The hinge point 30 is a ball 34 and a socket 36 that are connected together to from the movable hinge point 30.

Figure 5:
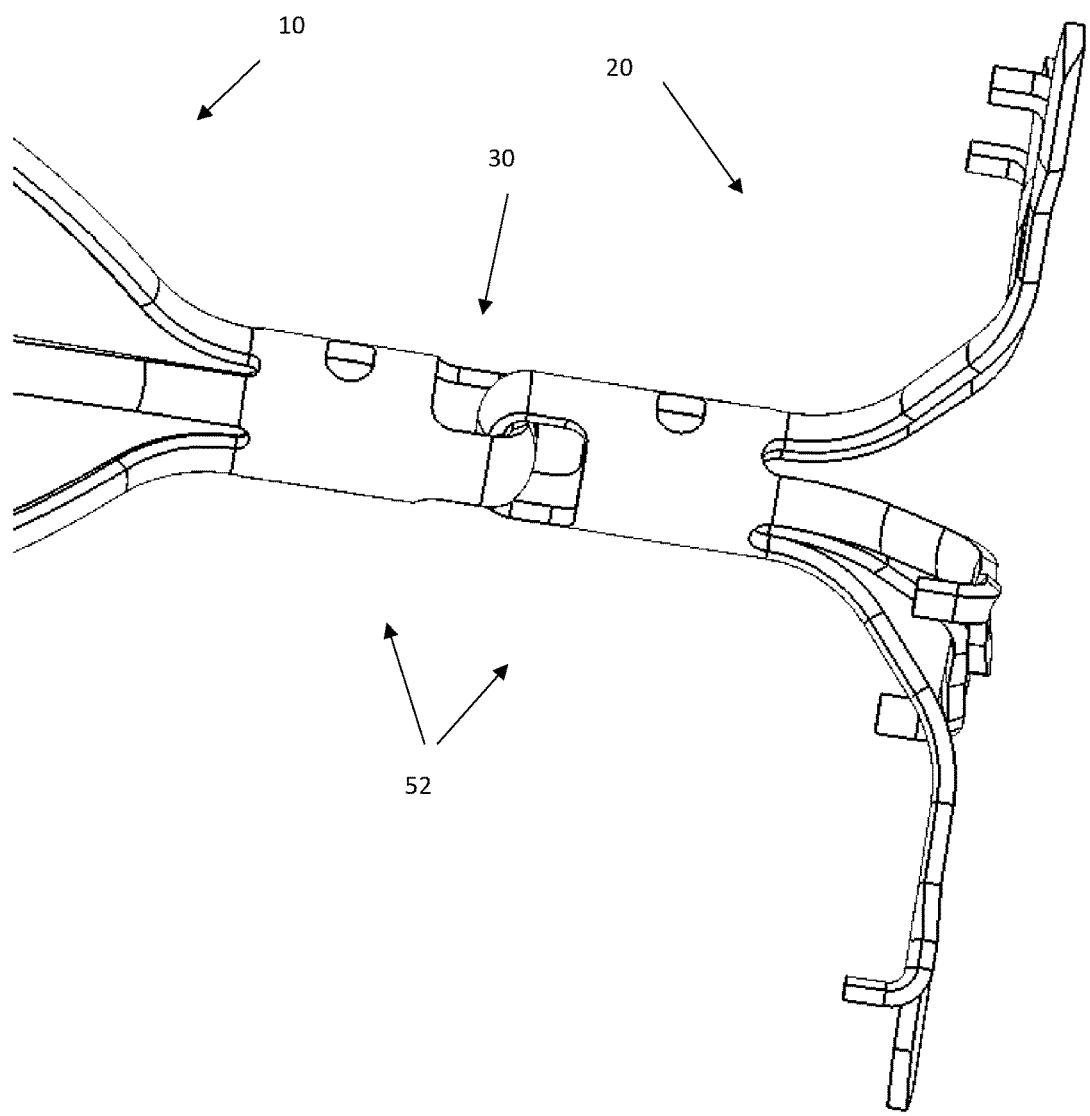
FIG. 5 illustrates a close-up view of a hinge.

FIG. 5 illustrates a close-up view of a hinge point 30 connecting two sections 52. The sections 52 include the valve section 10 and the anchor section 20 so that they are movable relative to each other.

Figure 6:
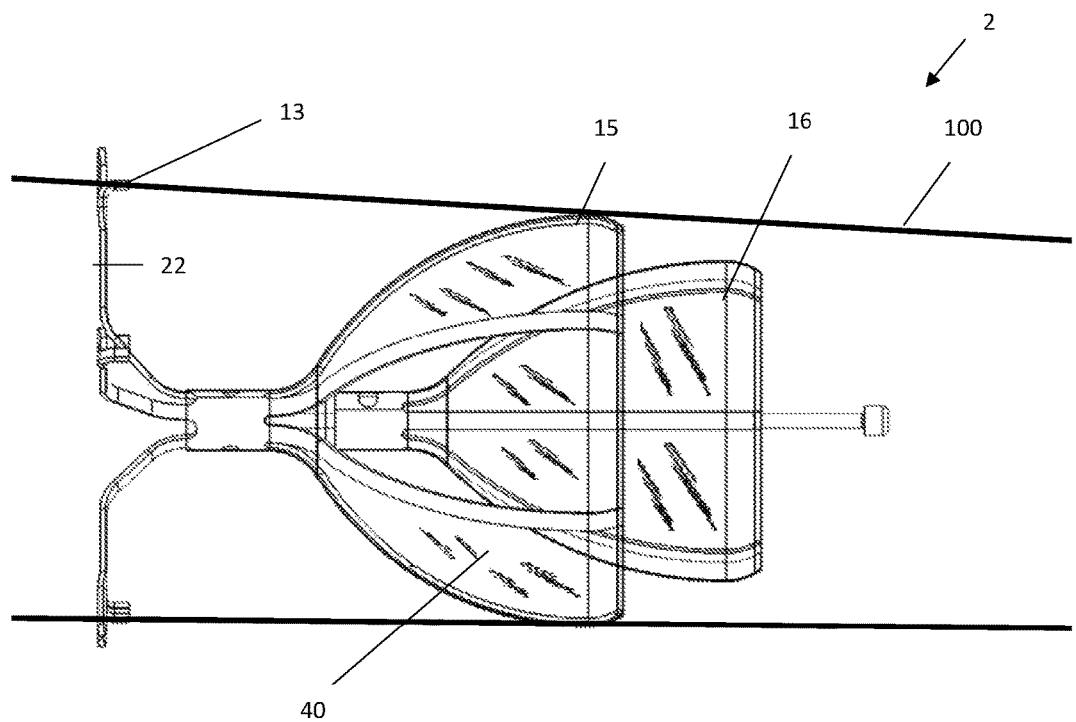
FIG. 6 illustrates a valve located within an airway.

FIG. 6 illustrates a side view of a valve 2 located within an airway 100. The arms 22 include anchor tips 13 that extend through the airway 100 and prevent further penetration through the airway 100 so that the valve 2 is retained in place. The valve also includes a first struct section 15 that includes a membrane 40 and a second struct section 16.

Figure 7:
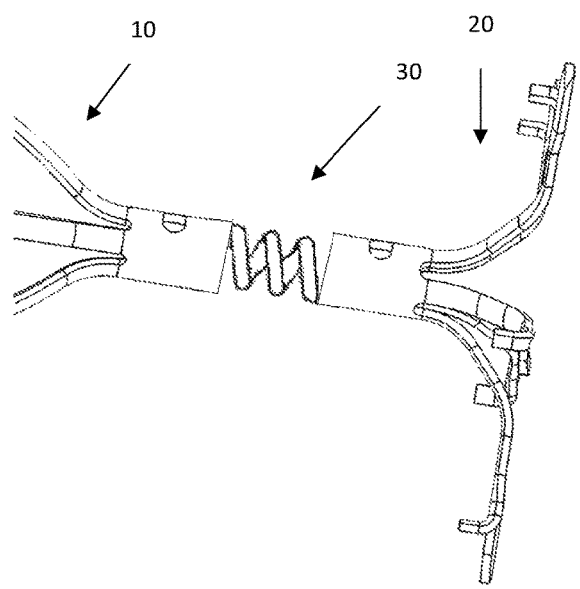
FIG. 7 illustrates an elevational view of a valve with a hinge.

FIG. 7 illustrates a valve section 10 and an anchor section 20 connected together via a hinge point 30, which as shown is a coil spring.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 valve
4 Distal End
6 Proximal End
10 valve section
12 strut
13 anchor tips
14 Rod
15 First Strut Section
16 Second Strut Section
18 Base member
20 Anchor section
22 Arms
24 Seal Section
30 Hinge point
32 Interconnect
34 Ball
36 Socket
40 membrane
50 Longitudinal axis
52 Sections
100 Airway

We claim:

1. A valve comprising:
   a. a rod,
   b. a plurality of struts in communication with the rod and extending generally radially outward away from the rod in a deployed state, the plurality of struts including at least:
      i. a plurality of first struts that extend radially outward from the rod a first distance, and
      ii. a plurality of second struts that extend radially outward a second distance from the rod, wherein the second distance is less than the first distance; and
   c. one or more membranes that are in communication with the first struts, the second struts, or both; and
   wherein one of the one or more membranes are in communication with the plurality of first struts, and a second of the one or more membranes is in communication with the plurality of second struts.

2. The valve of claim 1, wherein the valve includes a distal end and a proximal end and the plurality of second struts are in communication with the rod at a location closer to the proximal end than the plurality of first struts are in communication with the rod.

3. The valve of claim 1, wherein the plurality of second struts and the plurality of first struts all have a length and the length of the plurality of first struts is equal to or less than the length of the plurality of second struts.

4. The valve of claim 1, wherein the plurality of first struts and the plurality of second struts are aligned.

5. The valve of claim 1, wherein the plurality of first struts and the plurality of second struts are offset relative to each other.

6. The valve of claim 1, wherein one or more base members connect the plurality of struts to the rod.

7. The valve of claim 6, wherein the plurality of first struts are connected to one of the one or more base members, and the plurality of second struts are connected to a second of the one or more base members.

8. The valve of claim 1, wherein the valve has a valve section and an anchor section.

9. The valve of claim 8, wherein the valve section and the anchor section are one unitary piece.

10. The valve of claim 8 wherein the valve section and the anchor section are connected by a hinge point that includes a pair of interconnects connected together.

11. The valve of claim 8, wherein the valve section and the anchor section are connected by a hinge point that is a ball and socket connected together.

12. The valve of claim 8, wherein the valve section and the anchor section are connected by a hinge point that is a coil spring.

13. The valve of claim 1, wherein the membrane has a modulus of elasticity of between 0.0100 GPa to 0.0200 GPa.

14. The valve of claim 1, wherein at least one of the materials of the membrane is silicone.

15. A valve comprising:
   a. a rod,
   b. a plurality of struts in communication with the rod and extending generally radially outward away from the rod in a deployed state, the plurality of struts including at least:
      i. a plurality of first struts that extend radially outward from the rod a first distance, and
      ii. a plurality of second struts that extend radially outward a second distance from the rod, wherein the second distance is less than the first distance; and
   c. one or more membranes that are in communication with the first struts, the second struts, or both;
   wherein the plurality of second struts support the one or more membranes when the plurality of first struts are compressed so that the one or more membranes are moved into contact with a structure and the valve forms a seal with the structure.

16. The valve of claim 15, wherein the plurality of second struts are free of the one or more membranes.

17. The valve of claim 15, wherein the valve includes a distal end and a proximal end and the plurality of second struts are in communication with the rod at a location closer to the proximal end than the plurality of first struts are in communication with the rod; wherein the valve has a valve section and an anchor section; and wherein at least one of the materials of the membrane is silicone.

18. The valve of claim 15, wherein the plurality of first struts and the plurality of second struts are aligned.

19. The valve of claim 17, wherein the valve section and the anchor section are one unitary piece.

20. The valve of claim 15, wherein the valve section and the anchor section are connected by a hinge point that is a coil spring.

21. A valve comprising:
   a. a rod,
   b. a plurality of struts in communication with the rod and extending generally radially outward away from the rod in a deployed state, the plurality of struts including at least:
      i. a plurality of first struts that extend radially outward from the rod a first distance, and
      ii. a plurality of second struts that extend radially outward a second distance from the rod, wherein the second distance is less than the first distance; and
   c. one or more membranes that are in communication with the first struts, the second struts, or both;
   wherein the one or more base members connect the one or plurality of struts to the rod; the one or more base members are a single base member; and both the plurality of second struts and the plurality of first struts are connected to the single base member.

22. The valve of claim 21, wherein the valve includes a distal end and a proximal end and the plurality of second struts are in communication with the rod at a location closer to the proximal end than the plurality of first struts are in communication with the rod; wherein the valve has a valve section and an anchor section; and wherein at least one of the materials of the membrane is silicone.

23. The valve of claim 22, wherein the valve section and the anchor section are one unitary piece.

24. The valve of claim 21, wherein the valve section and the anchor section are connected by a hinge point that includes a pair of interconnects connected together.

* * * * *